(12) United States Patent
Guevremont

(10) Patent No.: US 7,378,651 B2
(45) Date of Patent: *May 27, 2008

(54) HIGH FIELD ASYMMETRIC WAVEFORM ION MOBILITY SPECTROMETER FAIMS

(75) Inventor: Roger Guevremont, Ottawa (CA)

(73) Assignee: Thermo Finnigan LLC, San Jose, CA (US)

( * ) Notice: Subject to any disclaimer, the term of this patent is extended or adjusted under 35 U.S.C. 154(b) by 102 days.

This patent is subject to a terminal disclaimer.

(21) Appl. No.: 10/529,307

(22) PCT Filed: Sep. 5, 2003

(86) PCT No.: PCT/CA03/01350

§ 371 (c)(1),
(2), (4) Date: Mar. 25, 2005

(87) PCT Pub. No.: WO2004/029603

PCT Pub. Date: Apr. 8, 2004

(65) Prior Publication Data

US 2006/0049363 A1 Mar. 9, 2006

Related U.S. Application Data

(60) Provisional application No. 60/413,162, filed on Sep. 25, 2002.

(51) Int. Cl.
*B01D 59/44* (2006.01)
*H01J 41/00* (2006.01)

(52) U.S. Cl. .................. 250/287; 250/281; 250/282; 250/283; 250/284; 250/285; 250/286; 250/288; 250/289; 250/290; 250/291; 250/292; 250/293; 250/294; 250/295; 250/296; 250/297; 250/298; 250/299; 250/300

(58) Field of Classification Search ........... 250/382, 250/291, 292, 281, 282, 283, 284, 285, 286, 250/287, 288, 289, 290, 293, 294, 295, 296, 250/297
See application file for complete search history.

(56) References Cited

U.S. PATENT DOCUMENTS 4,286,158 A * 8/1981 Charpak et al. ............ 250/374

(Continued)

*Primary Examiner*—Christine Sung
(74) *Attorney, Agent, or Firm*—Freedman & Associates

(57) ABSTRACT

Disclosed is an apparatus for separating ions including a plurality of first electrode portions, each first electrode portion of the plurality of first electrode portions having a first length and an outer surface that is at least partially curved in a direction transverse to the first length. The apparatus also includes a plurality of second electrode portions arranged in an alternating sequence with the plurality of first electrode portions, each second electrode portion of the plurality of second electrode portions having a second length and an outer surface that is curved in a direction transverse to the second length, a space between the outer surface of a first electrode portion and the outer surface of an adjacent second electrode portion defining a portion of an analytical gap for separating ions. At least an electrical controller is provided for electrically coupling to at least one of the plurality of first electrode portions and the plurality of second electrode portions, for applying an asymmetric waveform voltage between the at least one of the plurality of first electrode portions and the plurality of second electrode portions and for applying a direct current voltage between the at least one of the plurality of first electrode portions and the plurality of second electrode portions so as to establish an electric field within the portion of the analytical gap. During use, ions propagating along a direction that is transverse to both the first length and the second length are separated in the portion of the analytical gap between the outer surface of the first electrode portion and the outer surface of the adjacent second electrode portion.

14 Claims, 8 Drawing Sheets

U.S. PATENT DOCUMENTS

| | | | |
|---|---|---|---|
| 4,485,307 A * | 11/1984 | Osborne et al. | 250/385.1 |
| 4,878,149 A * | 10/1989 | Stiehl et al. | 361/230 |
| 4,999,501 A * | 3/1991 | Lacy | 250/385.1 |
| 5,420,424 A * | 5/1995 | Carnahan et al. | 250/287 |
| 5,789,745 A | 8/1998 | Martin et al. | |
| 6,169,287 B1 * | 1/2001 | Warburton | 250/370.1 |
| 6,204,087 B1 * | 3/2001 | Parker et al. | 438/56 |
| 6,333,504 B1 * | 12/2001 | Lingren et al. | 250/370.01 |
| 6,495,823 B1 | 12/2002 | Miller et al. | |
| 6,504,149 B2 | 1/2003 | Guevremont et al. | |
| 6,621,077 B1 | 9/2003 | Guevremont et al. | |
| 6,639,213 B2 | 10/2003 | Gillig et al. | |
| 6,727,496 B2 | 4/2004 | Miller et al. | |
| 6,744,043 B2 | 6/2004 | Loboda | |
| 6,770,875 B1 | 8/2004 | Guevremont et al. | |
| 6,781,132 B2 * | 8/2004 | McGregor | 250/370.09 |
| 6,806,466 B2 | 10/2004 | Guevremont et al. | |
| 6,825,461 B2 | 11/2004 | Guevremont et al. | |
| 2001/0032929 A1 | 10/2001 | Fuhrer et al. | |
| 2006/0097156 A1 * | 5/2006 | Guevremont | 250/290 |
| 2006/0151694 A1 * | 7/2006 | Guevremont et al. | 250/292 |

* cited by examiner

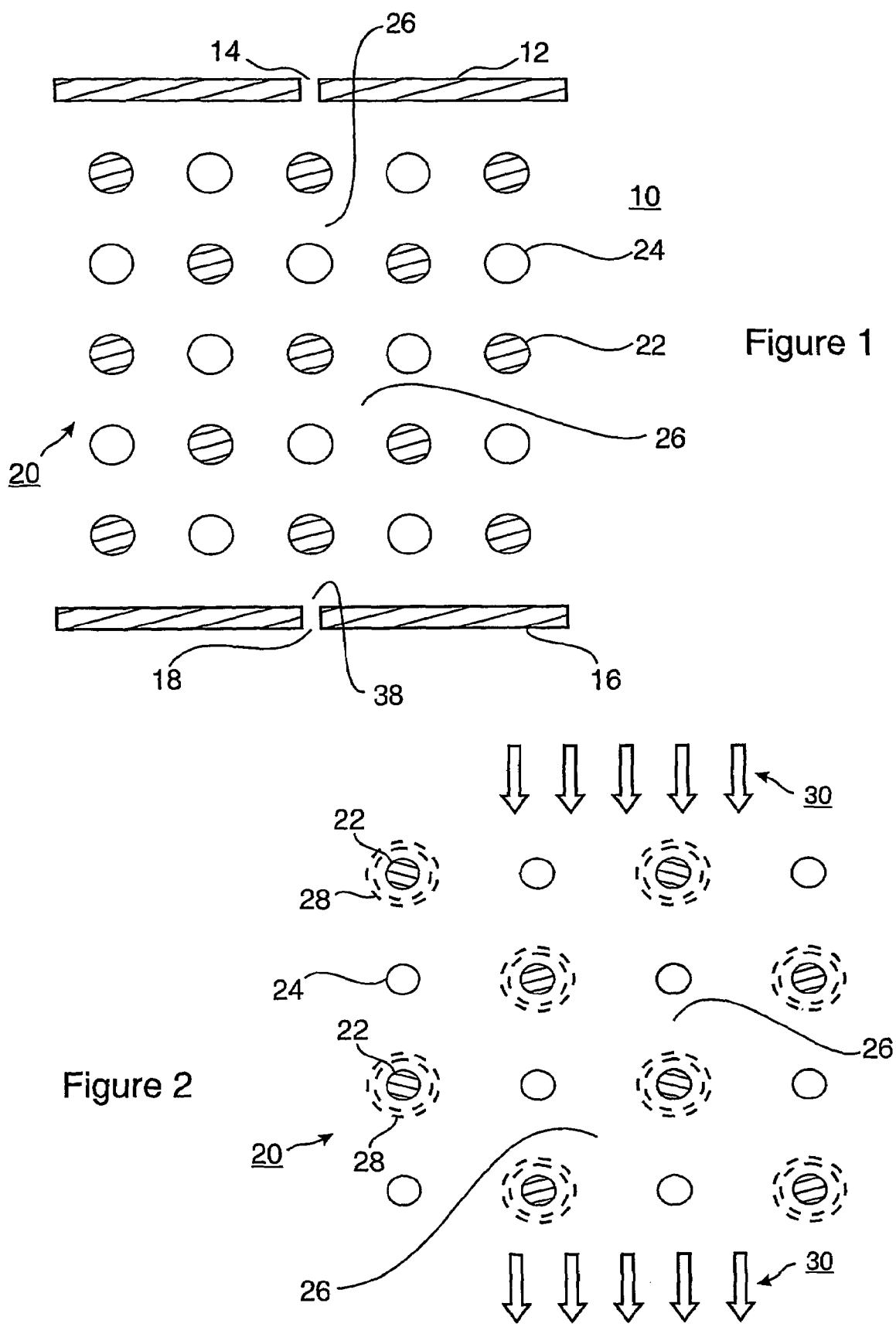

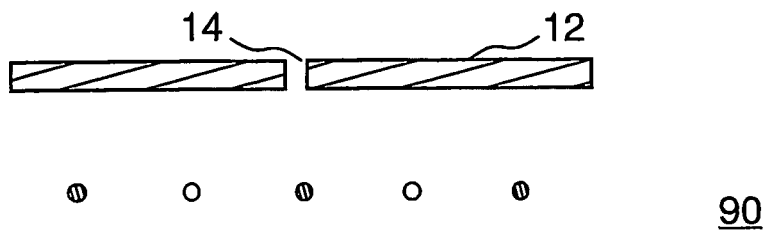
Figure 6a
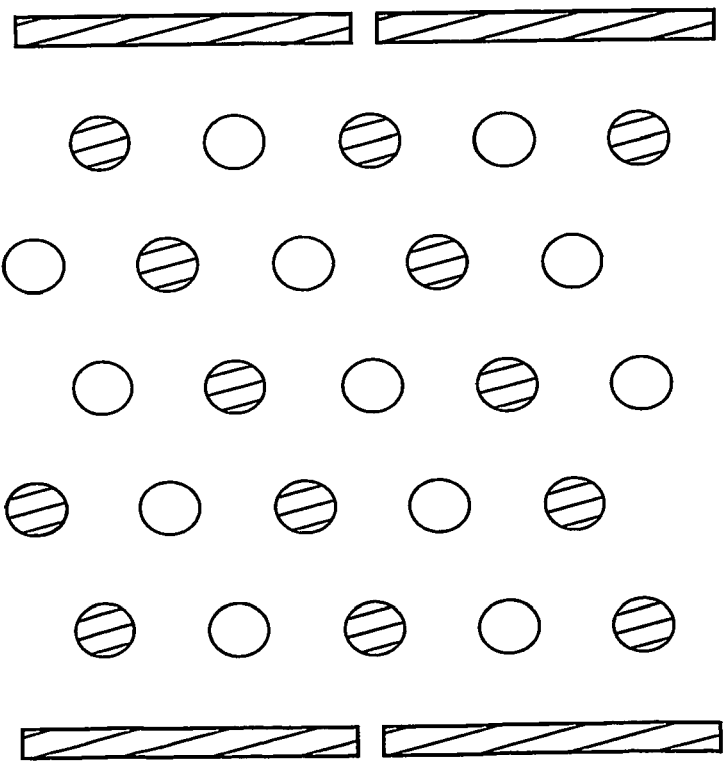
Figure 6b

HIGH FIELD ASYMMETRIC WAVEFORM ION MOBILITY SPECTROMETER FAIMS

This application claims the benefit of U.S. Provisional Application No. 60/413,162, filed Sep. 25, 2002.

FIELD OF THE INVENTION

The instant invention relates generally to a high field asymmetric waveform ion mobility spectrometer, more particularly the instant invention relates to a high field asymmetric waveform ion mobility spectrometer including an array of rod-shaped electrodes.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, N.Y., 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform voltage V(t) applied to it. The asymmetric waveform voltage V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 µs followed by −1000 V for 20 µs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform an ion moves with a y-axis velocity component given by $v_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = K E_L$, where K is the low field ion mobility under operating pressure and temperature conditions. The distance traveled is $d_L = v_L t_L = K E_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position relative to the y-axis. For example, if a positive ion travels farther during the positive portion of the waveform, for instance $d_H > d_L$, then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

A plurality of different electrode configurations are known in the art for establishing the electric fields that are required in order to separate ions according to the FAIMS principle. A non-exhaustive list of the known electrode configurations includes: concentric cylinders; parallel flat plates; parallel curved plates; concentric spheres; and a quadrupolar arrangement of parallel rods including an analytical gap defined in a direction along the length of the rods.

SUMMARY OF THE INVENTION

In accordance with an aspect of the instant invention there is provided an apparatus for separating ions comprising: a plurality of first electrode portions, each first electrode portion of the plurality of first electrode portions having a first length and an outer surface that is curved in a direction transverse to the first length; a plurality of second electrode portions interleaved in a repeating sequence with the plurality of first electrode portions, each second electrode portion of the plurality of second electrode portions having a second length and an outer surface that is curved in a direction transverse to the second length, a space between the outer surface of a first electrode portion and the outer surface of an adjacent second electrode portion defining a portion of an analytical gap for separating ions; and, at least an electrical controller for electrically coupling to at least one of the plurality of first electrode portions and the plurality of second electrode portions, for applying an asymmetric waveform voltage between the plurality of first electrode portions and the plurality of second electrode portions and for applying a direct current voltage between the plurality of first electrode portions and the plurality of second electrode portions so as to establish an electric field within the portion of the analytical gap, whereby ions propagating along a direction that is transverse to both the first length and the second length are separated in the portion of the analytical gap between the outer surface of the first electrode portion and the outer surface of the adjacent second electrode portion.

In accordance with another aspect of the instant invention there is provided an apparatus for separating ions comprising: a housing including a first surface and a second surface spaced-apart from the first surface and facing the first surface, an inlet aperture defined within the first surface and an outlet aperture defined within the second surface; a plurality of rod-shaped electrodes disposed between the first surface and the second surface such that each rod-shaped electrode of the plurality of rod-shaped electrodes is approximately parallel to both the first surface and the second surface, each rod-shaped electrode of the plurality of rod-shaped electrodes having a length and being spaced-apart from an adjacent rod-shaped electrode, so as to define an analytical gap extending between the inlet aperture and the outlet aperture for allowing ions to propagate therebetween along a direction of travel that is transverse to the length; and, at least an electrical controller for electrically coupling to at least some rod-shaped electrodes of the plurality of rod-shaped electrodes, for establishing an electric field within the analytical gap by the application of an asymmetric waveform voltage to the at least some rod-shaped electrodes of the plurality of rod-shaped electrodes and by the application of a direct current voltage to one of the at least some rod-shaped electrodes of the plurality of rod-shaped electrodes and other rod-shaped electrodes of the plurality of rod-shaped electrodes.

In accordance with yet another aspect of the instant invention there is provided an apparatus for separating ions comprising: a first formed-electrode including a plurality of rod-shaped first electrode portions; a second formed-electrode including a plurality of rod-shaped second electrode portions, the second formed-electrode for being mounted relative to the first formed-electrode such that an approximately same spacing is maintained between a rod-shaped first electrode portion of the plurality of rod-shaped first electrode portions and each adjacent rod-shaped second electrode portion of the plurality of rod-shaped second electrode portions; and, at least an electrical controller for electrically coupling to at least one of the first formed-electrode and the second formed-electrode, for applying an asymmetric waveform voltage between the first formed-electrode and the second formed-electrode and for applying a direct current voltage between the first formed-electrode and the second formed-electrode, so as to establish an electric field therebetween.

BRIEF DESCRIPTION OF THE DRAWINGS

Exemplary embodiments of the invention will now be described in conjunction with the following drawings, in which similar reference numbers designate similar items:

FIG. 1 is a simplified schematic view of a FAIMS analyzer including an array of rod-shaped electrodes according to an embodiment of the instant invention, taken along a first direction;

FIG. 2 is a schematic view of a portion of the FAIMS analyzer of FIG. 1, taken along the first direction;

FIG. 6a is a simplified schematic view of a FAIMS analyzer according to an embodiment of the instant invention including a plurality of wire electrodes;

FIG. 6b is a simplified schematic view of a FAIMS analyzer according to an embodiment of the instant invention including an array of rod-shaped electrodes in a first closest packing arrangement;

DETAILED DESCRIPTION OF THE DRAWINGS

Figure 3:
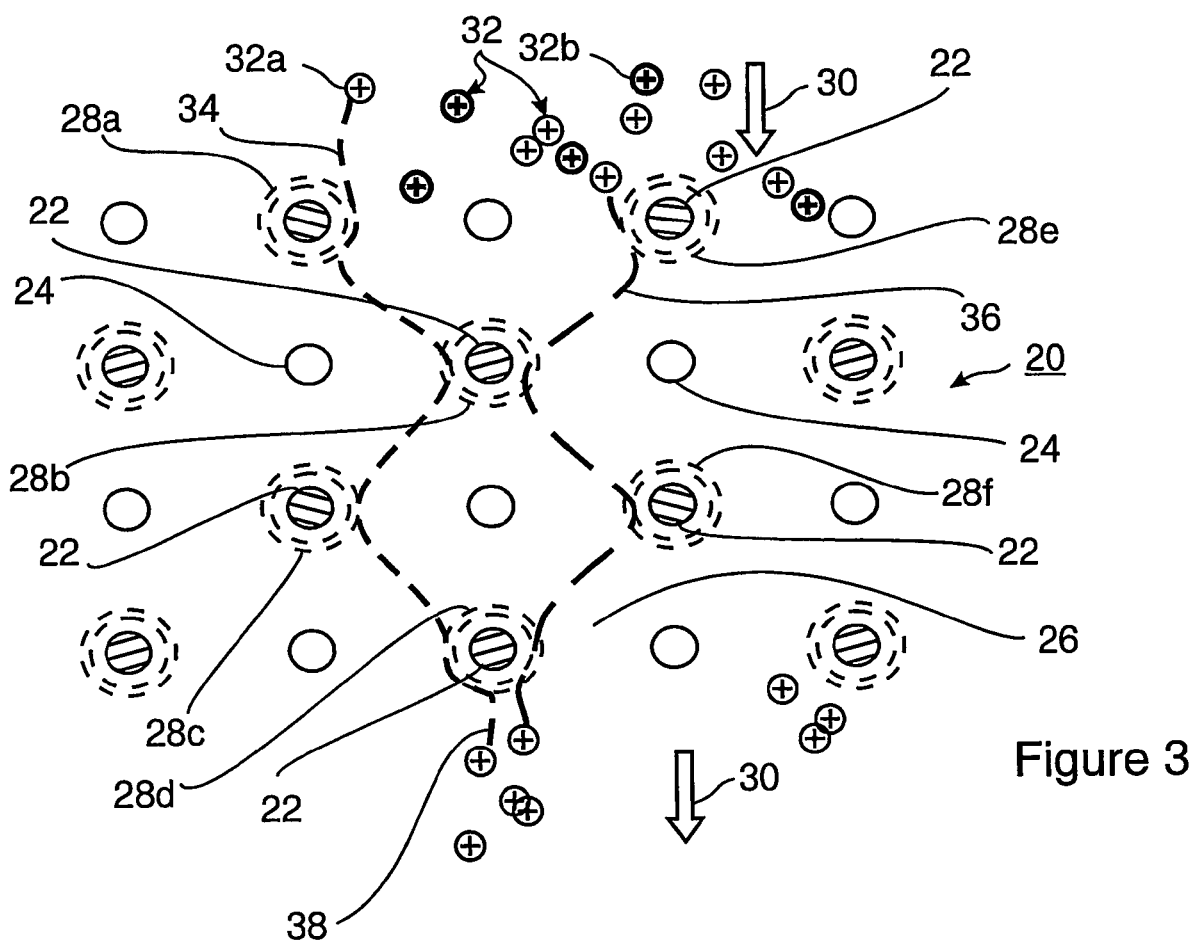
FIG. 3 illustrates the effect of electric fields within the FAIMS analyzer of FIG. 1 on the trajectory of ions.

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Referring to FIG. 1, shown is a simplified schematic view of a FAIMS analyzer including an array of rod-shaped electrodes according to an embodiment of the instant invention, taken along a first direction. In FIG. 1, the first direction is along the length of rod-shaped electrodes of the array. The FAIMS analyzer, which is shown generally at 10 in FIG. 1, includes an ion inlet plate 12 with an ion inlet 14, and an ion outlet plate 16 with an ion outlet 18. A not illustrated electrically insulating material supports the plates 12 and 16 in a spaced-apart parallel arrangement, one relative to the other. A plurality of rods, shown generally at 20 in FIG. 1, is disposed within the space between the ion inlet plate 12 and the ion outlet plate 16. The plurality of rods 20 is supported by the not illustrated electrically insulating material in a spaced-apart arrangement, so as to define an analytical gap 26 between adjacent rods for allowing ions that are introduced via the ion inlet 14 to propagate in a direction generally toward the ion outlet 18. Those portions of the plurality of rods 20 that are adjacent to, and that define the analytical gap 26 are referred to generally as "electrode portions".

Preferably, individual rods are arranged approximately parallel one to another, but it is to be understood that small deviations from parallel are also envisaged. As will be obvious to one of skill in the art, a plurality of different ion paths exists between the ion inlet 14 and the ion outlet 18. Furthermore, ions travelling along different ion paths may travel different distances between the ion inlet 14 and the ion outlet 18, as some of the different ion paths through the plurality of rods 20 are more torturous than others.

For ease of discussion, a second direction in the FAIMS analyzer is defined by the vertical path between the ion inlet 14 and the ion outlet 18 and a third direction is defined to be normal to both the first and second directions. Referring again FIG. 1, the third direction is the width (left to right) of the electrode array.

Preferably, the rods are relatively long in the first direction compared to the second direction so as to minimize the number of ions that approach the electrically insulating material supporting the rods. Ions hitting the electrically insulating material create a charged surface thereon. Electrical discharges within the FAIMS analyzer should be avoided as they may create burn tracks in the insulating material which can act as short circuits. Electrical discharges may also lead to chemical contamination of the FAIMS analyzer caused by the degradation of the insulating material.

Individual rods of the plurality of rods 20 are categorized into two different types of rods 22 and 24, which are identified conveniently by the electric voltages applied to them using a not illustrated electrical controller. Rods 22, shown as crosshatched circles in FIG. 1, have electrical connectors through which an asymmetric waveform is applied. The remaining rods 24 are shown as open circles in FIG. 1. A dc voltage is applied to either or both of rods 22 and rods 24 so that a dc potential difference, identically referred to as the compensation voltage, exists between the two types of rods. Each type of rod corresponds to one of the first or second electrode of a FAIMS analyzer. Furthermore, the rods 22, the rods 24, the ion inlet plate 12 and the ion outlet plate 16 have electrical connectors through which a dc voltage is applied. Alternately the electrical connectors may be used to set any of rods 22, rods 24, the ion inlet plate 12 and the ion outlet plate 16 at ground potential. The dc voltages applied to each one of the rods 24, the ion inlet plate 12 and the ion outlet plate 16 are not necessarily identical, since the ion inlet plate 12 preferably is biased to "push" ions in a direction toward the plurality of rods 20, whilst the ion outlet plate 16 preferably is biased to "pull" ions away from the plurality of rods 20 and in a direction toward the ion outlet 18. Of course, many other possible combinations of applying the dc voltages and the asymmetric waveform voltage to the individual rods of the FAIMS analyzer 10 will be apparent to one of skill in the art. It should be understood that the above example is intended to serve as a specific and non-limiting example to facilitate a more complete understanding of the instant invention.

Referring still to FIG. 1, preferably a flow of a gas is provided, during use, between a region proximate the ion inlet 14, through the plurality of rods 20, and out of the device 10 via ion outlet 18. Preferably, the FAIMS analyzer is substantially gas tight so that the majority of gas exits via the ion outlet 18. Ions that are entrained in the flow of a gas are carried through the analytical gap 26 between adjacent rods, toward a region 38 adjacent the ion outlet 18, and out through ion outlet 18 along with the flow of a gas. Since the FAIMS analyzer 10 transports and separates ions based upon the FAIMS principle, only a sub-set of the ions that are introduced through the ion inlet 14 are selectively transported to the ion outlet 18. A portion of the selectively transported ions pass through the ion outlet 18, and may be transported to one of an ion detection system, another ion mobility spectrometer, or alternatively to a mass spectrometer for further analysis.

Referring now to FIG. 2, shown is schematic view of a portion of the FAIMS analyzer of FIG. 1, taken along the first direction. Elements labeled with the same numerals have the same function as those illustrated at FIG. 1. For the purpose of discussing FIG. 2, it is assumed that the asymmetric waveform with peak voltage DV and the dc compensation voltage (CV) are both applied to rods 22, whilst rods 24 are maintained at ground potential. Of course, other combinations of applying the DV and CV will be envisaged by one of skill in the art.

Referring still to FIG. 2, application of the DV and CV to the rods 22 establishes an electric field within the analytical gap 26 between adjacent rods. The electric field that is established between any two adjacent rods includes a variable component relating to the application of the asymmetric waveform voltage, and a constant in time component relating to the applied dc voltage. Furthermore, the application of the asymmetric waveform voltage results in an electric field that is stronger in one polarity than in the other. Since the mobility of an ion may be higher or lower in the stronger field than in the lower field of opposite polarity, the oscillation of the ion may cause it to drift towards one of the rods. The dc component of the electric field is applied in order to counteract, or compensate, for this drift. Under the correct combination of applied asymmetric waveform voltage and applied dc voltage difference between the rods, ions with an appropriate ratio of mobility at high electric field strength to mobility at low electric field strength are in a balanced condition. In other words, the electric field arising from the applied CV just matches the drift effect caused by application of the waveform with peak voltage DV. For an ion with an appropriate field-dependence of the ratio of mobility at high field strength to mobility at low field strength, the application of the DV and CV to the rods 22, with the other rods 24 held at ground potential, results in a focusing region 28 surrounding each one of the rods 22.

The focusing region 28 around each rod 22 is defined in terms of the motion of the ions in the vicinity of this region. If, for example, an ion of interest is closer to the rod 22 than to the focusing region 28, the effect of the asymmetric waveform voltage is to push the ion away from the rod 22. Alternatively, if the ion is located beyond the focusing region 28, the ion tends to move generally towards the rod 22. In other words, the focusing region 28 is located a distance from the rod 22 at which the effect of the waveform that pushes the ions away from the rod 22 is exactly balanced by the attractive force towards rod 22 caused by the compensation voltage. Although this balance point actually is an infinitely thin two-dimensional surface, the regions 28 surrounding each electrode 22 are illustrated in FIG. 2 with an exaggerated thickness in recognition of the fact that ions oscillate within the electric field, and therefore are distributed over some range of distances from the rod 22. In addition, the ions are also under the influence of diffusion, ion-ion repulsion, etc., which cause the ions to be located over some finite range of distances rather than being compressed within the infinitely thin two-dimensional surface.

In the absence of a gas flow through the plurality of rods 20, the ions are expected to migrate to and collect within the focus regions 28 around the rods 22 to which the DV and CV are applied. Moreover, the ions become distributed at all locations equally around the circumference of the focus region 28. Accordingly, a flow of a gas 30 is provided through the analytical gap 26 between the rods, to transport the ions through the analytical gap 26 and toward the ion outlet 18. The introduction of a flow of gas 30 results in one of two possible changes to the distribution of ions within the plurality of rods 20, depending upon the rate of the flow of a gas. At low flow rates, the ions are directed around the circumference of the rods 22 following the curvature of the focus region 28. In effect, the flow of a gas 30 pushes the ions predominantly to the downstream side of the rods 22. This is possible because there are no barriers to motion of the ions around the focus region 28. At higher gas flow rates, the ions are no longer constrained to the focus regions 28, but instead are pulled out of the focus region 28 by the movement of the flow of a gas 30. Advantageously, the gas flow 30 carries selectively transmitted ions away from the plurality of rods 20 and toward the ion outlet 18.

Referring now to FIG. 3, illustrated is the effect of electric fields within the FAIMS analyzer of FIG. 1 on the trajectory of ions. Elements labeled with the same numerals have the same function as those illustrated at FIG. 1 and FIG. 2. For the purpose of discussing FIG. 3, it is once again assumed that the asymmetric waveform voltage with peak voltage DV and the dc compensation voltage (CV) are both applied to rods 22, whilst rods 24 are maintained at ground potential. In particular, the peak voltage DV is of positive polarity, whereas the CV is of negative polarity. Of course, other combinations of applying the DV and CV will be envisaged easily by one of skill in the art.

Ions 32 are produced at a not illustrated ionization source, such as for example one of an electrospray ionization source, a corona discharge ionization source, a radioactive nickel foil ionization source, and a MALDI ionization source. Typically, the ions 32 include at least two different types of ions, such as for example an ion of interest 32a and an ion that is other than of interest 32b. The ions 32 introduced into the FAIMS analyzer become entrained in the flow of a gas 30, which carries the ions into the analytical gap 26 between adjacent rods of the plurality of rods 20. Ions with the correct behavior at high electric field relative to low electric field are selectively transmitted through the analytical gap 26, whilst other types of ions collide with the rods and are lost. To this end, conditions are selected within the FAIMS analyzer 10 for transmitting the ions of interest 32a through the analytical gap 26.

Two simplified ion trajectories are shown in FIG. 3 in order to better illustrate the behavior of the ions within the analytical gap 26 of the FAIMS analyzer 10. Here, and elsewhere, the rapid oscillations of the ion due to the applied asymmetric waveform voltage are not shown on the trajectory. In the instant example, the flow of gas 30 through the plurality of rods 20 is sufficiently rapid to pull the ions away from the focus regions 28 around the rods 22. In general, positive ions 32 approaching the rods 22,24 are pulled in a direction toward the rods 22 as a result of the CV of negative polarity (for example) that is applied to the rods 22. An ion moving along ion trajectory 34 approaches a first focus region 28a of one of the rods 22. The flow of a gas 30 directs the ion around the rod 22 following the focus region 28a, until the ion eventually escapes from the focus region 28a. The combined effect of the gas flow 30 and the electric field is to move the ion away from the first focus region 28a and toward a second focus region 28b. Provided the ion does not collide with an electrode, the ion eventually traverses the plurality of rods 20 in a step wise fashion, moving from focus region 28b to 28c, from focus region 28c to 28d, and from focus region 28d to the ion outlet 18 of FIG. 1. Other ions move along other trajectories, such as for example trajectory 36, in an analogous manner.

Referring still to FIG. 3, the two trajectories 34 and 36 pass through the focus region of the same rod 22 in the vicinity of the region 38. Ions moving along the trajectories 34 and 36 are much closer to each other within the region 38 than when they entered the plurality of rods 20. Accordingly, the FAIMS analyzer 10 serves to "funnel" the selectively transmitted ions into a relatively narrow region of space for extraction through the ion outlet 18. Advantageously, this funnelling effect increases ion transmission efficiency by minimizing ion loss as a result of collisions with the ion outlet plate 16. Furthermore, the flow of a gas 30 can be used to assist in this funnel effect if the gas flows through the plurality of parallel rods 20 towards a single ion outlet 18. Optionally, this funneling effect is further enhanced by establishing a potential gradient within the FAIMS analyzer 10, for example by the application of different dc voltages to different rods 24 of the plurality of rods 20 across the width of the FAIMS analyzer for directing the ions generally toward the center of FIG. 3. Further optionally, ion trajectories are manipulated by the application of predetermined dc voltages to different rods 24, so as to establish an appropriate potential gradient for affecting ion trajectories in a desired manner.

Figure 4:
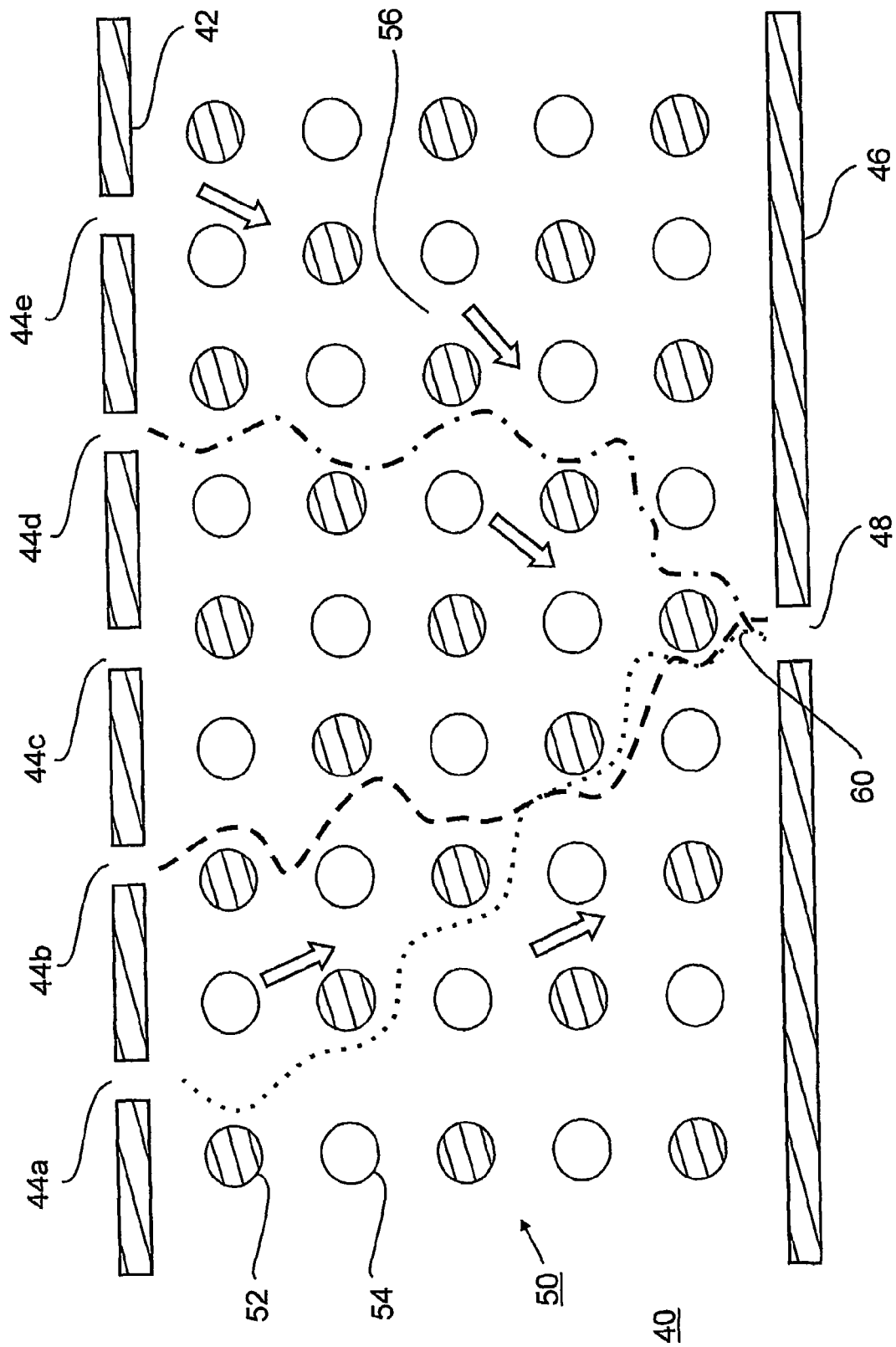
FIG. 4 is a simplified schematic view of another FAIMS analyzer including an array of rod-shaped electrodes according to another embodiment of the instant invention, taken along the first direction.

Referring now to FIG. 4, shown is a simplified schematic view of another FAIMS analyzer including an array of rod-shaped electrodes according to another embodiment of the instant invention, taken along a first direction. In FIG. 4, the first direction is along the length of rod-shaped electrodes of the array. The FAIMS analyzer, which is shown generally at 40 in FIG. 4, includes a plurality of ion inlets 44a, 44b, 44c, 44d, and 44e that are provided in an ion inlet plate 42, and a single ion outlet 48 is provided in an ion outlet plate 46. A not illustrated electrically insulating material supports the plates 42 and 46 in a spaced-apart parallel arrangement, one relative to the other. A plurality of rods, shown generally at 50, is disposed within the space between the ion inlet plate 42 and the ion outlet plate 46. The plurality of rods 50 is supported by the not illustrated electrically insulating material in a spaced-apart arrangement, so as to define an analytical gap 56 between adjacent rods for allowing ions that are introduced via the plurality of ion inlets 44a, 44b, 44c, 44d, and 44e to propagate in a direction generally toward the ion outlet 48.

Individual rods of the plurality of rods 50 are categorized into two different types of rods 52 and 54, which are identified conveniently by the electric voltages applied to them using a not illustrated electrical controller. Rods 52, shown as crosshatched circles in FIG. 4, have electrical connectors through which an asymmetric waveform voltage is applied. The remaining rods 54 are shown as open circles in FIG. 4. A dc voltage is applied to either or both of rods 52 and rods 54 so that a dc potential difference, identically referred to as the compensation voltage, exists between the two types of rods. Each type of rod corresponds to one of the first or second electrode of a FAIMS analyzer. Furthermore, the rods 52, the rods 54, the ion inlet plate 42 and the ion outlet plate 46 have electrical connectors through which a dc voltage is applied. Alternately the electrical connectors may be used to set any of rods 52, rods 54, the ion inlet plate 42 and the ion outlet plate 46 at ground potential. The dc voltages applied to each one of the rods 54, the ion inlet plate 42 and the ion outlet plate 46 are not necessarily identical, since the ion inlet plate 42 preferably is biased to "push" ions in a direction toward the plurality of rods 50, whilst the ion outlet plate 46 preferably is biased to "pull" ions away from the plurality of rods 50 and in a direction toward the ion outlet 48. Of course, many other possible combinations of applying the dc voltages and the asymmetric waveform voltage to the individual rods of the FAIMS analyzer 40 will be apparent to one of skill in the art. It should be understood that the above example is intended to serve as a specific and non-limiting example to facilitate a more complete understanding of the instant invention.

Referring still to FIG. 4, the funnel effect that was described above is shown being used to advantage. Ions introduced through each different ion inlet 44a, 44b, 44c, 44d, and 44e follow a different trajectory, three such trajectories are shown in FIG. 4, which converge toward the single ion outlet 48 in ion outlet plate 46. The arrows in FIG. 4 represent gas flowing through the FAIMS analyzer 40. For example, a flow of gas is introduced through each of the ion inlets 44a, 44b, 44c, 44d, and 44e along with the ions. Optionally, supplemental gas flows are introduced through not illustrated gas inlets disposed along the sides of the parallel-rod array FAIMS analyzer 40. Since there is only one outlet from the FAIMS analyzer 40, all gas flows through the device, and consequently all ion trajectories, tend to converge at region 60 adjacent to the ion outlet 48. Advantageously, near the ion inlet plate 42 the ions are spread out over a large volume of space, thereby minimizing ion-ion repulsion and space-charge forces. As the ions move along the different trajectories through the analytical gap 56, some ions collide with the rods and are lost. In particular, those ions that are other than of interest are lost relatively rapidly. Simultaneously, the ions moving along the different trajectories are "funneled" toward a smaller volume of space 60 prior to being extracted through the ion outlet 48. Since the number of ions that reach the volume of space 60 is small relative to the number of ions that are introduced into the analyzer 40 via ion inlets 44a, 44b, 44c, 44d, and 44e, ion-ion repulsion and space-charge forces within the volume of space 60 are minimized. Optionally, this funneling effect is further enhanced by establishing a potential gradient within the FAIMS analyzer 40, for example by the application of different dc voltages to different rods 54 of the plurality of rods 50. In this way, for example, ions are guided generally toward the single ion outlet 48 in ion outlet plate 46. Further optionally, ion trajectories are manipulated within other regions of the FAIMS analyzer 40 by the application of predetermined dc voltages to different rods 54, so as to establish an appropriate potential gradient for affecting ion trajectories in a desired manner.

Figure 5:
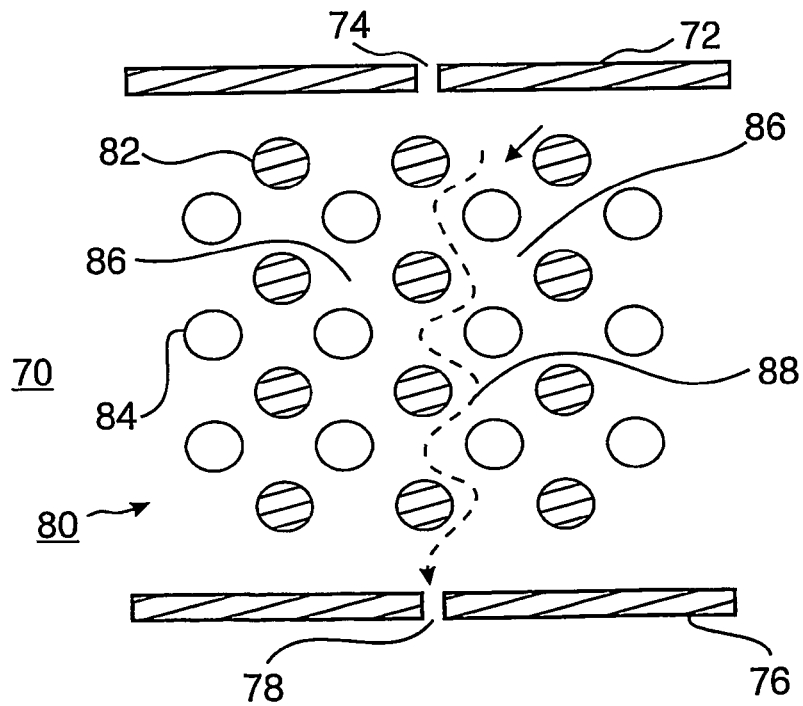
FIG. 5 is a simplified schematic view of yet another FAIMS analyzer including an array of rod-shaped electrodes according to yet another embodiment of the instant invention, taken along the first direction.

Referring now to FIG. 5, shown is a simplified schematic view of yet another FAIMS analyzer including an array of rod-shaped electrodes according to yet another embodiment of the instant invention, taken along the first direction. In FIG. 5, the first direction is along the length of rod-shaped electrodes of the array. The FAIMS analyzer, which is shown generally at 70 in FIG. 5, includes an ion inlet plate 72 with an ion inlet 74, and an ion outlet plate 76 with an ion outlet 78. A not illustrated electrically insulating material supports the plates 72 and 76 in a spaced-apart parallel arrangement, one relative to the other. A plurality of rods, shown generally at 80, is disposed within the space between the ion inlet plate 72 and the ion outlet plate 76. The plurality of rods 80 is supported by the not illustrated electrically insulating material in a spaced-apart arrangement, so as to define an analytical gap 86 between adjacent rods for allowing ions that are introduced via the ion inlet 74 to propagate in a direction generally toward the ion outlet 78. As will be obvious to one of skill in the art, a plurality of different ion paths exists between the ion inlet 74 and the ion outlet 78. Furthermore, ions travelling along different ion paths may travel different distances between the ion inlet 74 and the ion outlet 78, as some of the different ion paths through the plurality of rods 80 are more torturous than others.

Individual rods of the plurality of rods 80 are categorized into two different types of rods 82 and 84, which are identified conveniently by the electric voltages applied to them using a not illustrated electrical controller. Rods 82, shown as crosshatched circles in FIG. 5, have electrical connectors through which an asymmetric waveform voltage is applied. The remaining rods 84 are shown as open circles in FIG. 5. A dc voltage is applied to either or both of rods 82 and rods 84 so that a dc potential difference, identically referred to as the compensation voltage, exists between the two types of rods. Each type of rod corresponds to one of the first or second electrode of a FAIMS analyzer. Furthermore, the rods 82, the rods 84, the ion inlet plate 72 and the ion outlet plate 76 have electrical connectors through which a dc voltage is applied. Alternately the electrical connectors may be used to set any of rods 82, rods 84, the ion inlet plate 72 and the ion outlet plate 76 at ground potential. The dc voltages applied to each one of the rods 84, the ion inlet plate 72 and the ion outlet plate 76 are not necessarily identical, since the ion inlet plate 72 preferably is biased to "push" ions in a direction toward the plurality of rods 80, whilst the ion outlet plate 76 preferably is biased to "pull" ions away from the plurality of rods 80 and in a direction toward the ion outlet 78. Of course, many other possible combinations of applying the dc voltages and the asymmetric waveform voltage to the individual rods of the FAIMS analyzer 70 will be apparent to one of skill in the art. It should be understood that the above example is intended to serve as a specific and non-limiting example to facilitate a more complete understanding of the instant invention.

Referring now to FIG. 1 and FIG. 5, it is clear that the placement of the rods is not important to the overall motion of the ions through a FAIMS analyzer according to the instant invention. Rather, it is the fact that the array of rods is symmetrical around each rod 22, 82 to which the asymmetric waveform voltage is applied. When such a condition is satisfied, the ions may travel in any direction that the gas is flowing and experience approximately identical conditions. This is illustrated by a comparison of FIG. 1 and FIG. 5. In particular, the rods in FIG. 5 are arranged in a second optional pattern, different from the cubic array shown in FIG. 1 by rotation of the symmetric pattern of rods by about 45 degrees. Of course, other angles of rotation are also envisaged.

Again referring to FIG. 5 illustrates an advantage of this particular arrangement of rods. In particular, the gas flow carries an ion from a focus region around a rod to which is applied the asymmetric waveform voltage, to a focus region around a next rod in the path of gas flow to which is applied the asymmetric waveform voltage. If the ion inlet 74 is aligned with one of the electrodes 82 to which the asymmetric waveform voltage and compensation voltages are applied, the ion can easily follow a trajectory 88 to the exit orifice 78. This undulating motion maximizes the ion's travel through focus regions and the ion transmission efficiency is very high, since no part of the trajectory permits the ion sufficient freedom to diffuse toward and collide with a rod. Trajectory calculations show that the fields are always moving the ions away from colliding with the rods.

In each of the above embodiments, electrodes are provided in the form of rods to which are applied the various electric voltages. Optionally, the electrodes are provided in the form of wires, or in the form of rods having a smaller diameter relative to the inter-rod spacing than has been described above. FIG. 6a shows a simplified schematic view of a FAIMS analyzer 90 according to an embodiment of the instant invention including a plurality of wire electrodes 92. Elements labeled with the same numerals have the same function as those illustrated at FIG. 1.

Figure 6C:
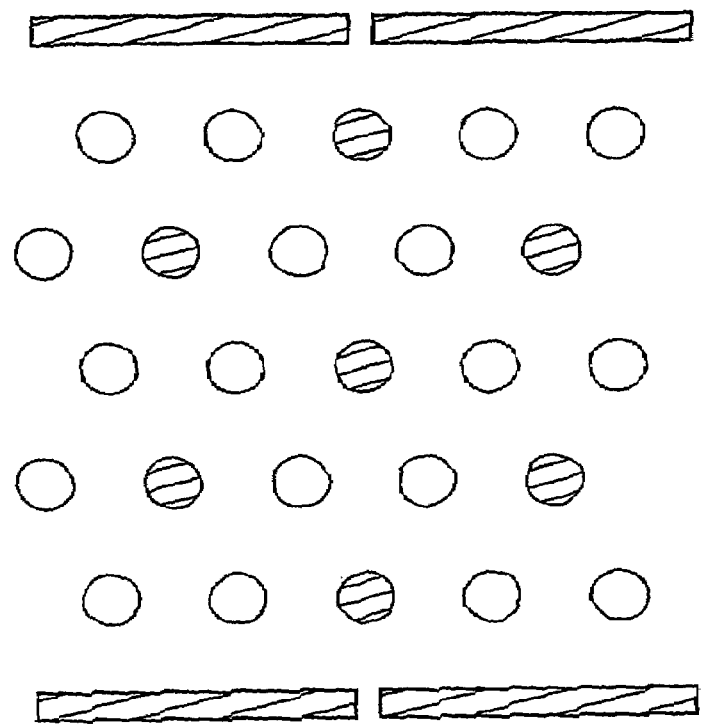
FIG. 6c is a simplified schematic view of a FAIMS analyzer according to an embodiment of the instant invention including an array of rod-shaped electrodes in a second closest packing arrangement.
Figure 6D:
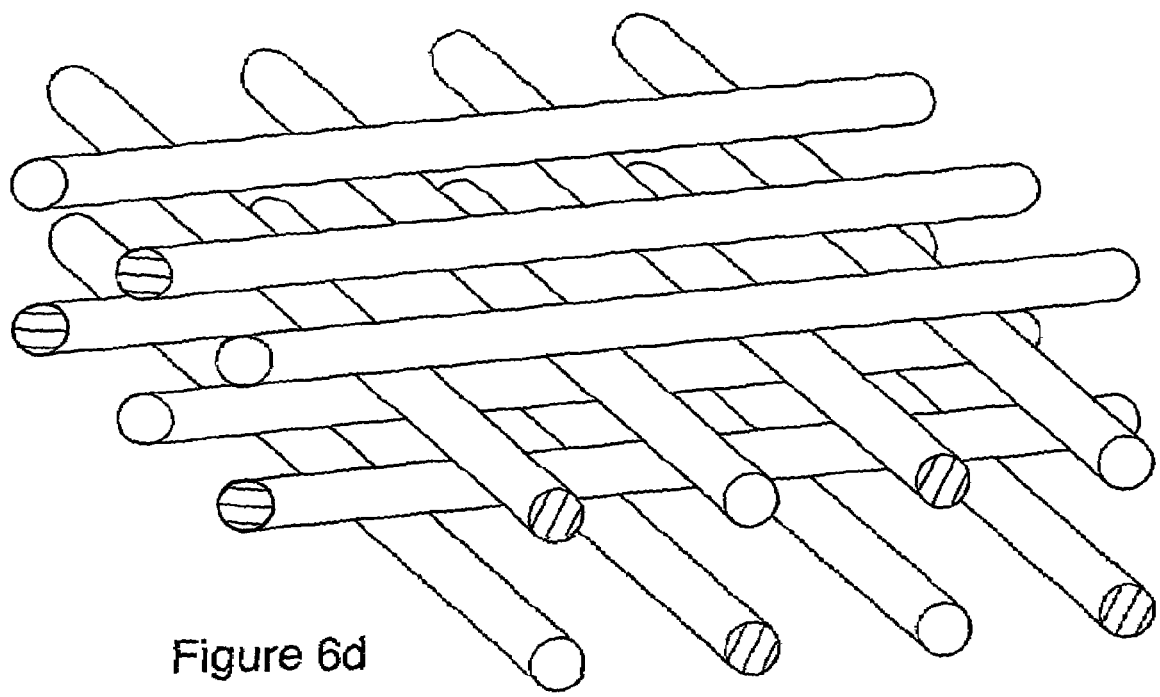
FIG. 6d is a simplified schematic view of a FAIMS analyzer according to an embodiment of the instant invention including a two-dimensional layered array of rod-shaped electrodes.
Figure 6E:
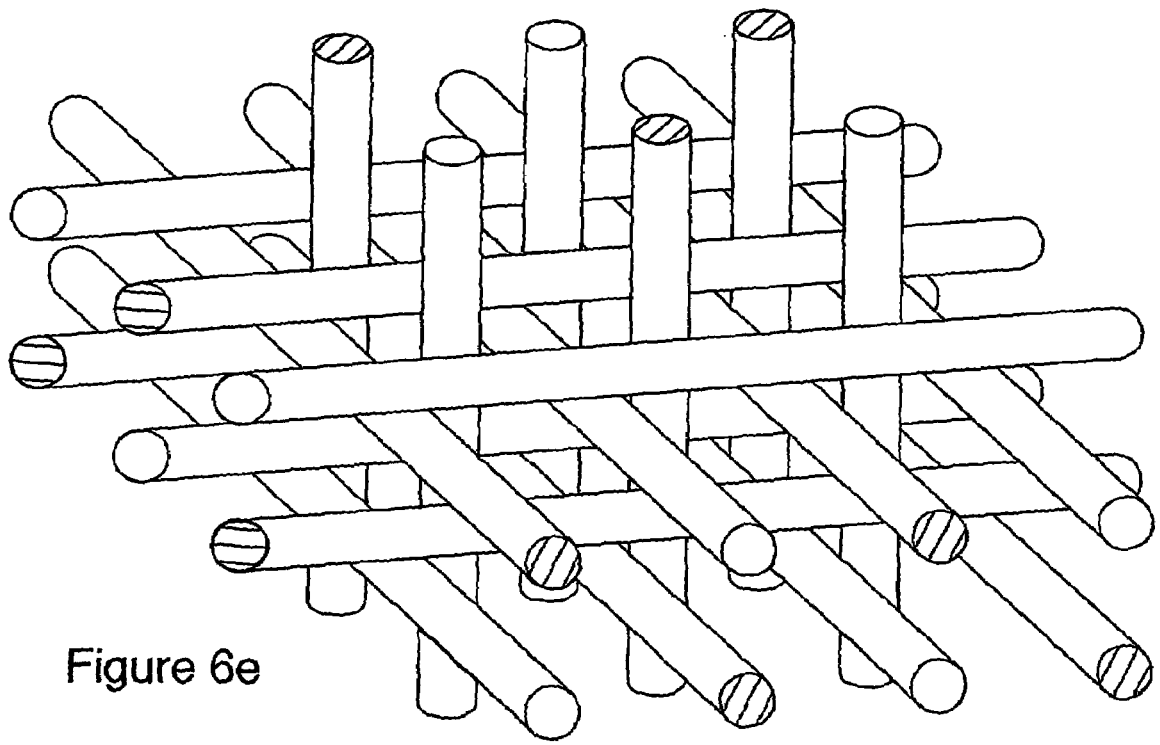
FIG. 6e is a simplified schematic view of a FAIMS analyzer according to an embodiment of the instant invention including a three-dimensional layered array of rod-shaped electrodes.

In yet another optional arrangement the rods may be close packed so that six other rods symmetrically surround each rod as shown for example at FIGS. 6b and 6c, or arranged in layers of rods where each layer is perpendicular to the next as shown at FIGS. 6d and 6e. Of course, other similar arrangements of the rods may be easily envisaged, without departing from the spirit and scope of the instant invention.

Further optionally, the rods that are shown in any of FIGS. 1 through 6e are other than circular in cross-section. For instance, optionally the rods are elliptical in cross section.

Still further optionally, the rods that are shown in any of FIGS. 1 through 6e are hollow and fabricated from a conductive material. Optionally, the rods include a non-conductive core that is one of hollow and solid, with a conductive outer surface.

Figure 7:
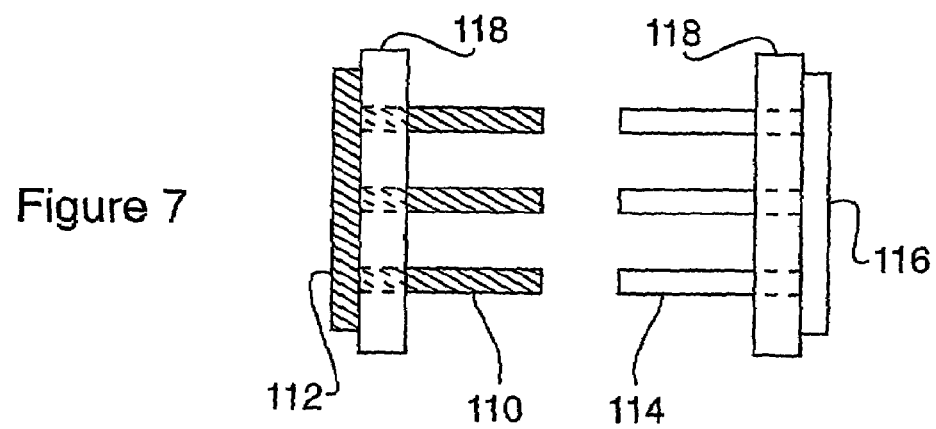
FIG. 7 is a simplified exploded view of yet another FAIMS analyzer including an array of rod-shaped electrodes according to the instant invention including two sets of electrode rods.

Referring now to FIG. 7, shown is a simplified exploded view of yet another FAIMS analyzer including an array of rod-shaped electrodes according to the instant invention, including two sets of electrode rods. In particular, a plurality of rods 110 is mounted to a same plate 112, which includes an electrical contact for connection, during use, to an electrical controller capable of applying an asymmetric waveform voltage to the same plate 112. Optionally, a CV is applied to the same plate 112 via an electrical contact. Similarly, a second plurality of rods 114 is mounted to a different plate 116, which includes an electrical contact for connection, during use, to an electrical controller capable of applying at least a dc voltage to the different plate 116. Advantageously, only a single electrical contact is require to apply the asymmetric waveform voltage to each rod of the plurality of rods 110 via the same plate 112. Similarly, only a single electrical contact is required to apply the dc voltage to each rod of the plurality of rods 114 via the different plate 116. Optionally, each rod of the plurality of rods 110 and each rod of the second plurality of rods 114 protrudes through an electrically insulating material 118, which supports the rods and maintains a desired spacing between the rods. Furthermore, the electrically insulating material insulates rods of the first plurality of rods 110 from the different plate 116, and insulates rods of the second plurality of rods 114 from the same plate 112. Optionally, a free end of each rod terminates at an electrically insulating endcap member.

Figure 8A:
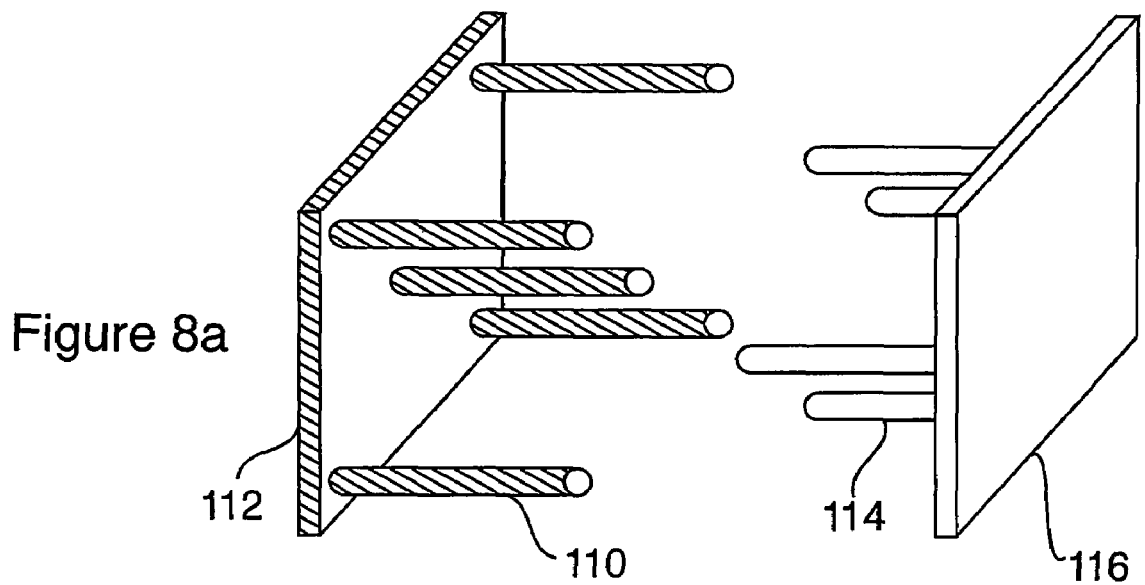
FIG. 8a is an exploded isometric view of the FAIMS analyzer of FIG. 7.
Figure 8B:
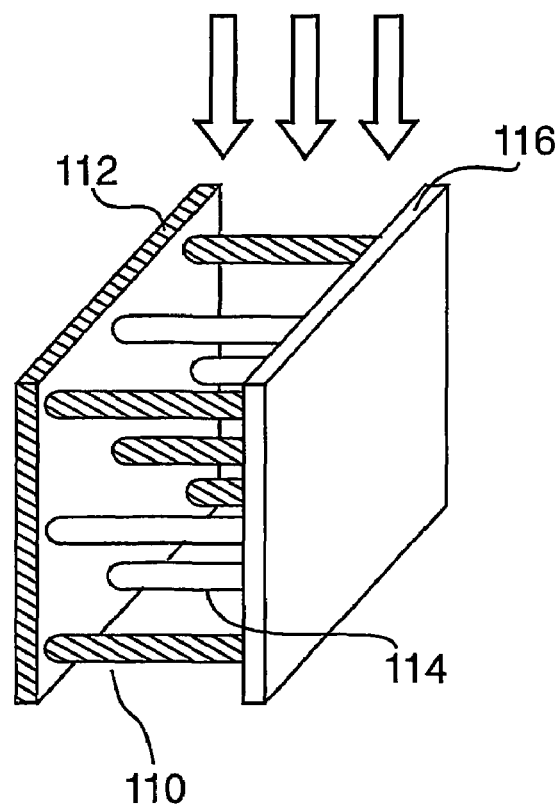
FIG. 8b is an isometric view of the FAIMS analyzer of FIG. 7.

Referring now to FIG. 8a, shown is an exploded isometric view of the FAIMS analyzer of FIG. 7. FIG. 8b shows an isometric view of the FAIMS analyzer of FIG. 7. The electrically insulating material 118 is omitted in FIGS. 8a and 8b for improved clarity. Rods of the first plurality of rods 110 are mounted to the same plate 112 and rods of the second plurality of rods 114 are mounted to the different plate 116 such that, when in the assembled condition shown in FIG. 8b, each rod of the first plurality of rods is adjacent to one or more rods of the second plurality of rods. The block arrows in FIG. 8b indicate the direction of gas flow through analyzer. Of course, rods mounted to one of the same plate 112 and the different plate 116 are electrically insulated from the other one of the same plate 112 and the different plate 116 such as optionally by the not illustrated insulating material 118.

Figure 9A:
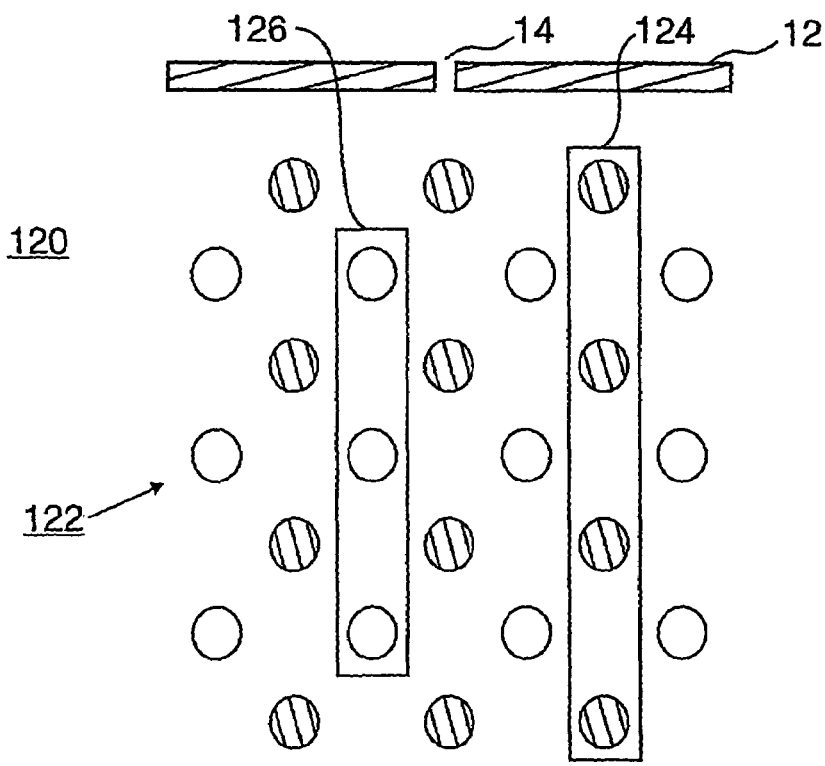
FIG. 9a is a simplified schematic view of a FAIMS analyzer including a formed electrode according to another embodiment of the instant invention, taken along a first direction; and, FIG. 9b is a simplified schematic view of the FAIMS analyzer of FIG. 9a taken along a direction normal to the first direction.

Referring now to FIG. 9a, shown is a simplified schematic view of a FAIMS analyzer including a formed electrode, taken along a first direction. The FAIMS analyzer, shown generally at 120, includes a not illustrated electrical controller that is connectable to an electrode assembly 122. The electrode assembly 122 includes formed electrodes, including a first type of formed electrode 124 and a second type of formed electrode 126. In the instant example, the first type of formed electrode 124 and the second type of formed electrode 126 are arranged approximately parallel one to the other, in a spaced-apart alternating sequence as shown in FIG. 9a. The first type of formed electrode 124 and the second type of formed electrode 126 are embedded within an electrically insulating material (not shown in FIG. 9a). The electrode assembly 122 is disposed between an ion inlet plate 12 including an ion inlet 14, and an ion outlet plate 16 including an ion outlet 18.

Figure 9B:
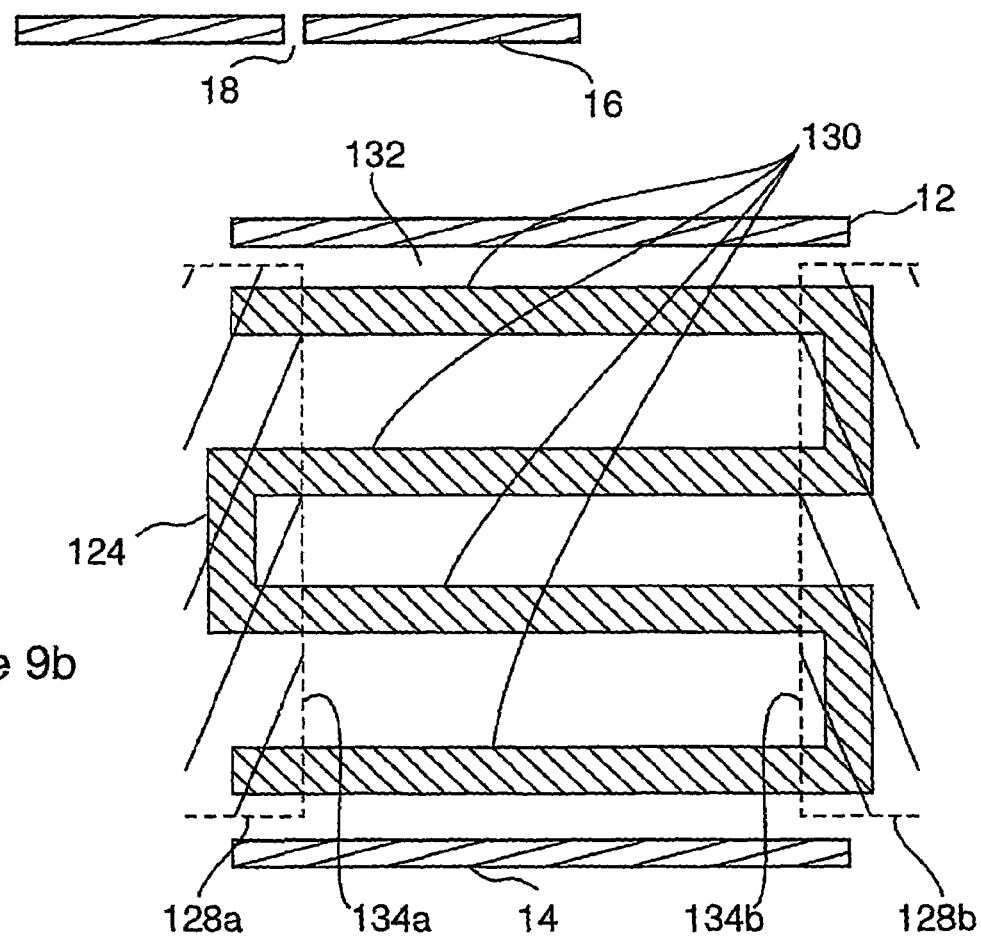

Referring now to FIG. 9b, shown is a simplified schematic view of the FAIMS analyzer of FIG. 9a taken along a second direction normal to the first direction. For the sake of clarity, only the first type of formed electrode 124 is shown in FIG. 9b. The first type of formed electrode 124 is shown embedded within an electrically insulating material 128a, 128b, such that a plurality of rod-shaped portions 130 of the first type of formed electrode 124 is disposed within a gap 132 between facing surfaces 134a, 134b of the electrically insulating material 128a, 128b, respectively. Of course, other combinations of formed electrodes and substantially rod-shaped electrodes may be envisaged by one of skill in the art.

Of course, different configurations of an electrical controller are envisaged as options for providing the asymmetric waveform voltage and the CV. Power sources may be combined in one housing or may be in the form of separately housed components. The electrical controller may include an electronic circuit, for instance to generate the asymmetric waveform, or may be a simple device such as an electrically conducting wire for maintaining an electrode at ground potential. The term electrical controller has been used to denote the means by which a desired voltage is applied and maintained on an electrode. Although the foregoing detailed description of the instant invention describes electrical voltages as being applied to specific electrodes of the various electrode assemblies, for example via electrical contacts carried on the specific electrodes, it is to be understood that the effect is to apply a desired voltage between electrodes so as to establish an electrical field for separating the ions. Of course, the strength of the electric field that is established is dependent upon the voltages that are applied between the electrodes, as well as the distance between the electrodes that are used to establish the fields.

Numerous other embodiments may be envisaged without departing from the spirit and scope of the instant invention.

What is claimed is:

1. A high field asymmetric waveform ion mobility spectrometer (FAIMS) apparatus for separating one type of ion from a mixture including a plurality of different types of ions, comprising:
    a plurality of first electrode portions, each first electrode portion of the plurality of first electrode portions having a first length and an outer surface that is at least partially curved in a direction transverse to the first length;
    a plurality of second electrode portions interleaved in a repeating sequence with the plurality of first electrode portions, each second electrode portion of the plurality of second electrode portions having a second length and an outer surface that is at least partially curved in a direction transverse to the second length, a space between the outer surface of a first electrode portion and the outer surface of an adjacent second electrode portion defining a portion of an analytical gap for separating the one type of ions from the mixture including the plurality of different types of ions; and,
    at least an electrical controller for electrically coupling to at least one of the plurality of first electrode portions and the plurality of second electrode portions, for applying an asymmetric waveform voltage between the plurality of first electrode portions and the plurality of second electrode portions and for applying a direct current voltage between the plurality of first electrode portions and the plurality of second electrode portions so as to establish an electric field within the portion of the analytical gap, whereby ions propagating along a direction that is transverse to both the first length and the second length are separated in the portion of the analytical gap between the outer surface of the first electrode portion and the outer surface of the adjacent second electrode portion.

2. An apparatus according to claim 1, wherein the plurality of first electrode portions comprises a plurality of first electrode rods, each first electrode rod of the plurality of first electrode rods defining one first electrode portion of the plurality of first electrode portions.

3. An apparatus according to claim 2, wherein the plurality of second electrode portions comprises a plurality of second electrode rods, each second electrode rod of the plurality of second electrode rods defining one second electrode portion of the plurality of second electrode portions.

4. An apparatus according to claim 1, wherein one of the plurality of first electrode portions and the plurality of second electrode portions comprises a formed-electrode.

5. An apparatus according to claim 1, wherein the plurality of first electrode portions comprises a first formed-electrode and wherein the plurality of second electrode portions comprises a second formed-electrode, the second formed-electrode for being mounted relative to the first formed-electrode such that an approximately same spacing is maintained between a first electrode portion of the plurality of first electrode portions and each adjacent second electrode portion of the plurality of second electrode portions.

6. An apparatus according to claim 5, wherein at least one of the first formed-electrode and the second formed-electrode is generally an extended S-shaped electrode.

7. An apparatus according to claim 5, wherein the first formed-electrode comprises a first electrode assembly including a first plurality of rods and a first support, a first end of each rod of the first plurality of rods being mounted to the first support such that each rod is approximately parallel to and spaced-apart from every other rod of the first plurality of rods.

8. An apparatus according to claim 7, wherein the second formed-electrode comprises a second electrode assembly including a second plurality of rods and a second support, a first end of each rod of the second plurality of rods being mounted to the second support such that each rod is approximately parallel to and spaced-apart from every other rod of the second plurality of rods, the second electrode assembly being mounted relative to the first electrode assembly such that an approximately same spacing is maintained between each rod of the first plurality of rods and an adjacent rod of the second plurality of rods.

9. An apparatus according to claim 1, wherein each first electrode portion is approximately circular in a cross-section taken through a plane that is normal to the length of the first electrode portion and wherein each second electrode portion is approximately circular in a cross-section taken through a plane that is normal to the length of the second electrode portion.

10. An apparatus according to claim 1, wherein each first electrode portion is approximately elliptical in a cross-section taken through a plane that is normal to the length of the first electrode portion and wherein each second electrode portion is approximately elliptical in a cross-section taken through a plane that is normal to the length of the second electrode portion.

11. A high field asymmetric waveform ion mobility spectrometer (FAIMS) apparatus for separating one type of ion from a mixture including a plurality of different types of ions, comprising:
    a housing including a first surface and a second surface spaced-apart from the first surface and facing the first surface, an inlet aperture defined within the first surface and an outlet aperture defined within the second surface;
    a plurality of rod-shaped electrodes disposed between the first surface and the second surface such that each rod-shaped electrode of the plurality of rod-shaped electrodes is approximately parallel to both the first surface and the second surface, each rod-shaped electrode of the plurality of rod-shaped electrodes having a length and being spaced-apart from an adjacent rod-shaped electrode, so as to define an analytical gap extending between the inlet aperture and the outlet aperture for allowing ions to propagate therebetween along a direction of travel that is transverse to the length; and, at least an electrical controller for electrically coupling to at least some rod-shaped electrodes of the plurality of rod-shaped electrodes, for establishing an electric field within the analytical gap by the application of an asymmetric waveform voltage to the at least some rod-shaped electrodes of the plurality of rod-shaped electrodes and by the application of a direct current voltage to one of the at least some rod-shaped electrodes of the plurality of rod-shaped electrodes and other rod-shaped electrodes of the plurality of rod-shaped electrodes.

12. An apparatus according to claim 11, wherein the rod-shaped electrodes of the plurality of rod-shaped electrodes are arranged such that each rod-shaped electrode to which the asymmetric waveform voltage is applied has as its nearest neighbor a rod-shaped electrode to which only the direct current voltage is applied.

13. An apparatus according to claim 11, wherein the inlet aperture is adapted for providing a flow of a gas into the housing, through the analytical gap and out of the outlet aperture, the flow of gas for transporting ions along the direction of travel that is transverse to the length.

14. An apparatus according to claim 11, wherein the first surface includes a plurality of inlet apertures for supporting introduction of ions into the analytical gap at a plurality of different locations along the first surface, each different location corresponding to a location of one of the plurality of inlet apertures, the plurality of inlet apertures including the inlet aperture defined within the first surface.

* * * * *